United States Patent [19]
Gifford

[11] Patent Number: 5,666,972
[45] Date of Patent: Sep. 16, 1997

[54] CONDOM AND PACKAGE

[76] Inventor: Henry Gifford, 230 Riverside Dr., #11C, New York, N.Y. 10025-6172

[21] Appl. No.: 437,558

[22] Filed: Jun. 6, 1995

[51] Int. Cl.$^6$ .................................................. A61F 6/02
[52] U.S. Cl. ........................... 128/842; 128/844; 206/69
[58] Field of Search ................................. 128/842, 844, 128/918; 604/347–353; 206/69

[56] References Cited

U.S. PATENT DOCUMENTS

| | | | |
|---|---|---|---|
| 2,321,254 | 6/1943 | Schmid | 206/69 |
| 4,840,188 | 6/1989 | Heidenfelder. | |
| 4,846,197 | 7/1989 | Benjamin | 604/353 |
| 5,044,492 | 9/1991 | Auerbach | 206/69 |

FOREIGN PATENT DOCUMENTS 2249295  5/1992  United Kingdom ................. 128/918

*Primary Examiner*—Michael A. Brown
*Attorney, Agent, or Firm*—Brumbaugh, Graves, Donohue & Raymond

[57] ABSTRACT

A condom package has a tactile means of identifying the orientation of the condom within the package. The tactile means is the shape or texture of the package. In another embodiment, the tactile means of identifying orientation is on the condom itself.

3 Claims, 2 Drawing Sheets

CONDOM AND PACKAGE

SPECIFICATION

BACKGROUND OF THE INVENTION

This invention relates to condoms as used by humans during sexual activities. More particularly, this invention relates to a means for determining the orientation of a condom so as to ensure proper application of the condom.

Typically, condoms are made of an elastic material, such as latex, and are packaged individually in a sealed plastic or foil pouch having an upper and a lower generally flat surface. When packaged, the condom is rolled in a manner such that it appears as a latex disk with a tubular edge.

Use of the condom typically involves opening the package, removing the condom from the package, visually determining the correct inside/outside orientation of the condom, and donning the condom. Condoms are orientation specific with regard to the direction in which they will unroll. However, if one tries to unroll a condom from the incorrect orientation, i.e., inside out, it is usually not apparent from the outset that an error is being made and difficult application may ensue.

Visual determination of orientation is often difficult and can be made more difficult by less than optimum ambient lighting conditions that may prevail at the time of use. This confusion increases the chances of accidently trying to apply the condom inside out.

It is a primary object of the present invention to provide an easy means of determining the proper orientation of a condom using only one's sense of touch. It is another object of the present invention to provide a means of determining the proper orientation of a condom using one's sense of sight.

SUMMARY OF THE INVENTION

In accordance with the present invention, a condom's orientation is identified by tactile and visual means on either the condom package or the condom itself, or both.

BRIEF DESCRIPTION OF THE DRAWINGS

Other objects, features and advantages of the invention will become apparent, and its construction and operation better understood, from the following detailed description when read in conjunction with the accompanying drawings, in which.

DETAILED DESCRIPTION

According to the present invention, when use of a condom in conditions not conducive to viewing the package or its contents is anticipated, the prospective user can become familiar with a tactile identification means on the outside of the unopened package prior to use. Written instructions on or accompanying the package can acquaint the prospective user ahead of time with the correlation between the orientation of the package and the orientation of the condom within. The prospective user can also make his own visual observation of the orientation of a condom after opening a package. The method of use of these tactile means includes feeling the tactile orientation identification on the package, removing the condom from the package, orienting the condom, and donning the condom.

Figure 1:
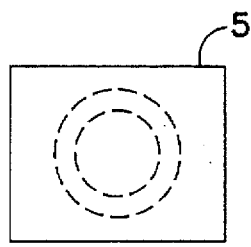
FIG. 1 is a plan view of a prior art condom rolled up inside it's package.
Figure 2:
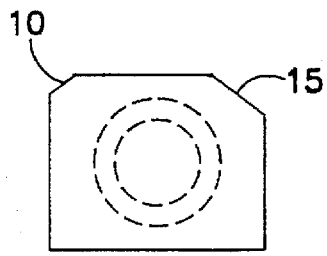
FIG. 2 is a plan view of a first embodiment of the invention wherein the condom package is generally square and is missing two corners.

FIG. 1 shows a typical prior art condom in its package 5. One cannot determine the orientation of the condom, i.e., which side is the inside and which is the outside, merely by looking at or touching the unopened package. FIG. 2 shows an embodiment of the present invention which includes a means of determining which side is which. In this embodiment, the means is the shape of the package which is generally square but has two clipped corners 10, 15, resulting in a six-sided package. By differing the size or shape of the clipped corners relative to one another, thereby rendering the package asymmetrical, the user can easily determine the orientation of the package either visually or by determining the contour of the package shape using only his sense of touch. Instructions on or accompanying the package will inform the prospective user that when the larger clipped corner 15 is in the upper right-hand position, for example, the inside of the condom is facing away from the prospective user.

Figure 3:
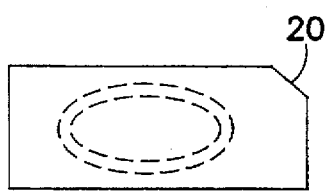
FIG. 3 is a plan view of a second embodiment of the invention wherein the condom package is generally rectangular and has one corner missing.

FIG. 3 shows an embodiment of the invention in which one corner 20 is missing from a rectangular package, resulting in an asymmetrical five-sided package. Instructions on or accompanying this package will inform the prospective user that when the clipped corner 20 is in the upper right-hand position, for example, the inside of the condom is facing away from the prospective user.

Figure 4A:
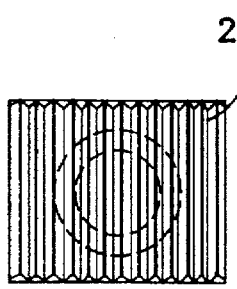
FIG. 4A is a plan view of the textured surface of a third embodiment of the invention wherein one surface of the condom package is textured and the other is smooth.
Figure 4B:
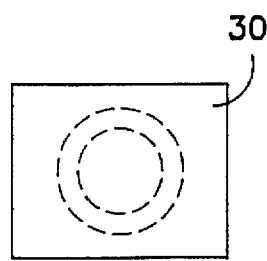
FIG. 4B is a plan view of the smooth surface of the third embodiment.
Figure 4C:
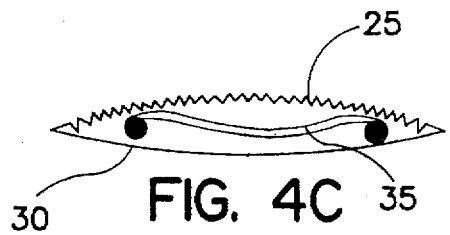
FIG. 4C is a cross-sectional view of the package of the third embodiment.

Another means of identifying the orientation of a condom within its package, other than by the shape of the package, is by texture. According to the present invention, one surface of a condom package is given a different texture than the other, for example, a corrugated texture. The textured surface will correspond to a particular side of the condom within the package, either the inside or the outside. This is shown in FIGS. 4A, 4B and 4C, where FIG. 4A is a plan view of the textured surface 25 of the package, FIG. 4B is a plan view of the smooth surface 30 of the package and FIG. 4C is a cross-sectional view of the package showing both the textured and smooth surfaces of the package as well as the condom 35 within.

Figure 5A:
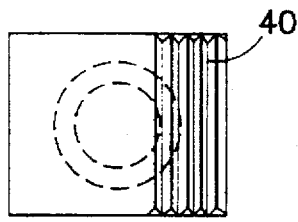
FIG. 5A is a plan view of the textured surface of a fourth embodiment of the invention wherein a portion of one surface of the condom package is textured and the remainder of the package is smooth.
Figure 5B:
FIG. 5B is a cross-sectional view of the package of the fourth embodiment.

Only one portion of one surface of the condom package need be of a different texture from the rest of the package. This is shown in FIGS. 5A and 5B, where FIG. 5A is a plan view of the surface which has a portion of a different texture 40 and FIG. 5B is a cross-sectional view of the package. Just as with the packaging-shape-dependent means of identifying orientation, the prospective user can become familiar with the significance of the texture-dependent means of identifying orientation prior to use by reading accompanying instructions or by observing the orientation of the condom within its package after opening the textured package.

Figure 6:
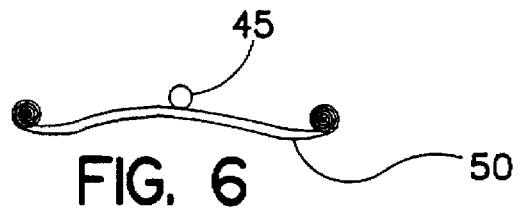
FIG. 6 is an side elevation view of a fifth embodiment of the invention wherein the tactile means of identifying the orientation of the condom is on the closed end of the rolled condom.

In yet another embodiment of the present invention, the means of identifying the orientation of the condom is located on the condom itself. FIG. 6 shows the rolled condom 50 with the identifier 45 which is on the outside of the condom. Upon removing the condom 50 from its package, the user can determine where the identifier 45 is either by sight or by using one or more fingers. Once the determination is made, the user can apply the condom, secure in the knowledge that it is being applied properly.

Figure 7:
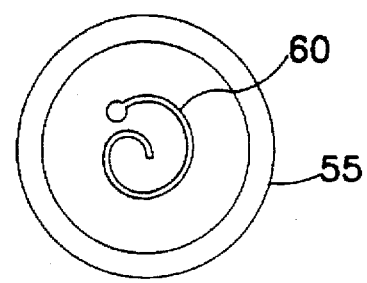
FIG. 7 is a plan view of a sixth embodiment of the invention wherein the tactile means of identifying the orientation of the condom is on the closed end of the rolled condom and has an orientation-specific shape.

In a variation of the previous embodiment, the identifier can be of an orientation-specific shape to further ensure that the user has correctly determined the inside/outside orientation of the condom. As an example, FIG. 7 shows a plan view of a rolled condom 55 with a clockwise swirl identifier 60 on the outside. If the user touches the identifier 60 from the inside, he will be able to quickly determine that he is feeling the inside, and not the outside, by following the contour of the identifier 60, which will be counterclockwise. Although slightly more intricate, use of the orientation-specific identifier 60 allows the identifier 60 to be of a smaller height than is necessary with the symmetrical identifier 45 shown in FIG. 6, since the sole identifying property of identifier 45 is its height above the condom surface.

Figure 8A:
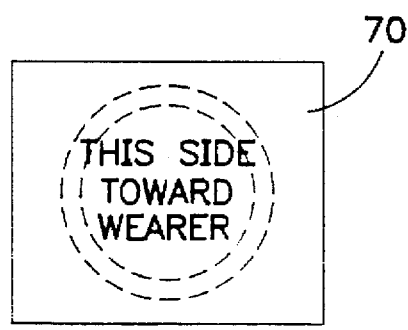
FIG. 8A is a plan view of a seventh embodiment of the invention wherein the condom package has printing on one surface and the condom within has a predetermined orientation with respect to the printed surface.
Figure 8B:
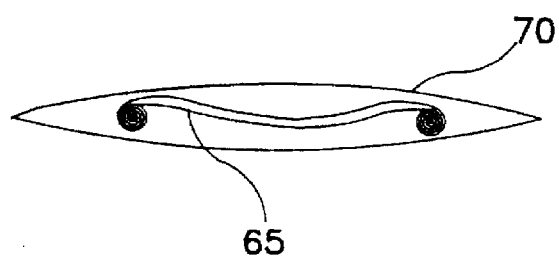
FIG. 8B is a cross-sectional view of the seventh embodiment.

According to the present invention, condom orientation may also be determined by printed means on a predetermined side of the condom package. FIGS. 8A and 8B depict an embodiment wherein the condom 65 is oriented with its inside adjacent to the package surface 70 which has the words "THIS SIDE TOWARD WEARER" printed thereon. Of course, any wording which conveys to the user the orientation of the condom within the package may be used. Thus, lighting conditions permitting, the user will then be able to quickly determine the proper orientation of the condom by merely glancing at the package.

While the above is a description of the invention in its preferred embodiments, various modifications, alternate constructions and equivalents may be employed. Therefore, the above description and illustration should not be taken as limiting the scope of the invention which is defined by the appended claims.

I claim:

1. A package for containing a condom having a correct orientation for proper application onto a user, said package comprising at least two generally flat surfaces each of a predetermined circumferential shape indicative of the correct orientation for proper application of the condom, wherein the predetermined circumferential shape is a square with two clipped corners, one larger than the other, resulting in an asymmetrical six-sided polygon.

2. A package for containing a condom having a correct orientation for proper application into a user, said package comprising at least two generally flat surfaces each of a predetermined circumferential shape indicative of the correct orientation for proper application of the condom, wherein the predetermined circumferential shape is a rectangle having one clipped corner, resulting in an asymmetrical five-sided polygon.

3. A condom comprising:

a cylindrical elastic casing having an open end and a closed end; and a tactile identifier located on the outside of the closed end of the elastic casing, said identifier having an orientation-specific shape in the form of a swirl.

\* \* \* \* \*